US012257379B2

(12) United States Patent
Roux et al.

(10) Patent No.: US 12,257,379 B2
(45) Date of Patent: Mar. 25, 2025

(54) MOBILE NEGATIVE PRESSURE WOUND THERAPY DEVICE

(71) Applicant: Mölnlycke Health Care AB, Gothenburg (SE)

(72) Inventors: Alain Roux, Träslövsläge (SE); Anders Hermansson, Mölnlycke (SE); Stefan Kidborg, Ytterby (SE)

(73) Assignee: Mölnlycke Health Care AB, Mölndal (SE)

( * ) Notice: Subject to any disclaimer, the term of this patent is extended or adjusted under 35 U.S.C. 154(b) by 0 days.

(21) Appl. No.: 17/998,981

(22) PCT Filed: May 24, 2021

(86) PCT No.: PCT/EP2021/063751
§ 371 (c)(1),
(2) Date: Nov. 16, 2022

(87) PCT Pub. No.: WO2021/239656
PCT Pub. Date: Dec. 2, 2021

(65) Prior Publication Data

US 2023/0211067 A1 Jul. 6, 2023

(30) Foreign Application Priority Data

May 25, 2020 (EP) .................................... 20176284

(51) Int. Cl.
*A61M 1/00* (2006.01)
*A61F 13/05* (2024.01)

(52) U.S. Cl.
CPC ............... *A61M 1/90* (2021.05); *A61F 13/05* (2024.01); *A61M 2205/3331* (2013.01); *A61M 2205/8206* (2013.01)

(58) Field of Classification Search
CPC ............ A61M 1/90; A61M 2205/3331; A61M 2205/8206; A61F 13/00068
See application file for complete search history.

(56) References Cited

U.S. PATENT DOCUMENTS 4,582,598 A * 4/1986 Bilstad ...................... G01F 1/76
210/101
6,636,010 B1 * 10/2003 Malmstrom ......... G05D 7/0676
318/672

(Continued)

FOREIGN PATENT DOCUMENTS

| | | |
|---|---|---|
| EP | 2438935 | 4/2012 |
| WO | WO2020/011690 | 1/2020 |

(Continued)

OTHER PUBLICATIONS

International Search Report and Written Opinion were mailed on Jul. 5, 2021 by the International Searching Authority for International Application No. PCT/EP2021/063751 filed on May 24, 2021 and published as WO 2021/239656 (Applicant—Molnlycke Health Care AB) (14 pages).

*Primary Examiner* — Susan S Su
*Assistant Examiner* — Katherine-Ph Minh Pham
(74) *Attorney, Agent, or Firm* — Ballard Spahr LLP

(57) ABSTRACT

The present disclosure generally relates to a mobile negative pressure wound therapy (NPWT) device comprising a negative pressure pump, where the NPWT device is adapted to ensure that an operation of the negative pressure pump is terminated if the NPWT device is operating outside of a predefined operational range. The present disclosure also relates to a corresponding method for operating such an NPWT device and a thereto related computer program product.

17 Claims, 4 Drawing Sheets

118
102
100
122
Batt
VP
Control circuitory
µ
120
110
112
126
116
114
104
106
108

(56) References Cited

U.S. PATENT DOCUMENTS

| | | | | |
|---|---|---|---|---|
| 9,737,649 | B2 | 8/2017 | Begin et al. | |
| 2010/0100075 | A1* | 4/2010 | Weston | A61M 1/74 604/543 |
| 2019/0328964 | A1* | 10/2019 | Desch | A61M 5/16859 |

FOREIGN PATENT DOCUMENTS

| | | | |
|---|---|---|---|
| WO | WO2020/043567 | 3/2020 | |
| WO | WO-2020043567 A1 * | 3/2020 | A61M 1/73 |

* cited by examiner

MOBILE NEGATIVE PRESSURE WOUND THERAPY DEVICE

CROSS-REFERENCE TO RELATED APPLICATIONS

This application is a U.S. National Phase Application of International Application No. PCT/EP2021/063751, filed May 24, 2021, which claims priority to European Patent Application No. 20176284.6, filed May 25, 2020, each of which is hereby incorporated by reference in its respective entirety.

TECHNICAL FIELD

The present disclosure generally relates to a mobile negative pressure wound therapy (NPWT) device comprising a negative pressure pump, where the NPWT device is adapted to ensure that an operation of the negative pressure pump is terminated if the NPWT device is operating outside of a predefined operational range. The present disclosure also relates to a corresponding method for operating such an NPWT device and a thereto related computer program product.

BACKGROUND

Negative pressure wound therapy (NPWT) is a technique that promotes healing of e.g. surgical, acute and chronic wounds by the application of a sub-atmospheric pressure to the wound, using a negative pressure pump. The NPWT technique also permits less outside disturbance of the wound as well as for transportation of excess fluids away from the wound site. Generally, the NPWT technique has until now mainly been applied to a patient while in a hospital environment. However, recent product development now allows the technique to be used by a patient in a home environment.

When an NPWT device is used in such a home environment, it may be possible that the NPWT device is not operated and monitored by professional users, as compared to when the NPWT device is used in the mentioned hospital environment. Thus, it is desirable to further simplify the operational use of the NPWT device, for minimizing any errors in use and handling.

One example of such an NPWT device is disclosed in U.S. Pat. No. 9,737,649, where the NPWT device can include one or more controllers responsible for various system functions associated with various levels of responsiveness, such as interfacing with a user (e.g., patient, physician, nurse, etc.), controlling a negative pressure pump, providing network connectivity, and the like. The NPWT device is in U.S. Pat. No. 9,737,649 furthermore configured to determine and monitor flow of fluid in the system, by using one or more pressure transducers or sensors that measure pressure in a fluid flow path and provide feedback to the one of the controllers. The NPWT device is also configured to provide indication, alarms, etc. reflecting operating conditions to a user, including for example visual, audible, tactile, and other types of indicators and/or alarms.

The solution presented in U.S. Pat. No. 9,737,649 generally improves the operation of the NPWT device for an "unskilled home user", by implementing means for ensuring that the NPWT device is easy to operate and effectively indicates to the user if there is a failure with the NPWT device.

Even though the solution U.S. Pat. No. 9,737,649 may reduce operational failure of an NPWT device for use in a home environment, there is always a desire to further improve the safety for the end user, i.e. the patient making use of the NPWT device, with the desire to minimize any risk involved with using an NPWT device.

Furthermore, in WO2020043567 there is presented apparatuses and methods for providing negative pressure wound therapy to multiple wounds, specifically for determining a presence of blockage in one or more fluid flow paths connecting a negative pressure source to one or more dressings can be performed.

Still further, in EP2438935 there is presented a negative pressure wound therapy apparatus can include a wound dressing, a fluid collection container, a vacuum pump comprising a pump motor, and tubing.

Additionally, in WO2020011690 there is presented a negative pressure wound therapy apparatus can include a first source of negative pressure and a first power source, the first source of negative pressure configured to supply, via a fluid flow path, negative pressure to a wound covered by a wound dressing, and the first power source configured to provide electrical power to the first source of negative pressure

SUMMARY

In view of above-mentioned and other drawbacks of the prior art, it is an object of the present disclosure to provide improvements in relation to efficient and safe operation of a NPWT device operating to establish a negative pressure within the sealed space formed by a wound cover in relation to a wound site.

According to an aspect of the present disclosure, it is therefore provided a mobile negative pressure wound therapy (NPWT) device, comprising a housing, a negative pressure pump arranged within the housing, a canister fluidly coupled to the negative pressure pump and to a wound cover, the wound cover provided for creating a sealed space defined in part by a wound site, a battery arranged within the housing, and a control unit arranged within the housing, the control unit being electrically connected to the battery and adapted to provide power to the negative pressure pump for operating the negative pressure pump to establish a negative pressure within the sealed space, wherein the NPWT device further comprises control circuitry provided externally from the control unit and adapted to terminate the operation of the negative pressure pump if the NPWT device is determined to operate outside of a predefined operational range.

The present disclosure is based upon the realization that further measures are needed to ensure that operation of the NPWT device is swiftly terminated in case the NPWT device starts to operate outside of what is a normal behavior, in accordance to the present disclosure defined as a predefined operational range. Enabling such a swift termination of operation of the NPWT device is in accordance to the present disclosure achieved by arranging the NPWT device to further comprise a control circuitry provided externally from the control unit. The external control circuitry is in line with the present disclosure arranged to not be dependent on a correct operation of the control unit (typically comprising some form of programmable circuit), meaning that the external control circuitry (typically comprising at least one logic gate or controllable switch provided with a first input control line for controlling the controllable switch) can terminate the operation of the NPWT device also in cases where e.g. software/firmware running at the control unit fails to operate in a fully normal manner. Accordingly, advantages following the present disclosure may for example include the possibility to provide an extra layer of security to the NPWT device to ensure that the user is not exposed to e.g. an unwanted action of the NPWT device in case of its failure. It should thus be stressed that the control circuitry provided externally from the control unit is generally not integrated with the control unit and thus provided as a completely separate circuit as compared to the control unit.

Further advantages following the present disclosure includes the possibility to allow the external control circuitry to directly receive an input from e.g. a sensor, and allow the sensor to directly influence if the operation of the NPWT device is to be terminated, without the need to first be processed by the control unit. Accordingly, the setup as defined in accordance to the present disclosure allows for a mixture of advanced processing using the control unit and the extra layer of security achieved by the external control circuitry in case of a failure in the operation of e.g. the control unit.

An example of an undesirable operation NPWT device is in case the negative pressure pump fails to stop once a pressure threshold has been reached. In a typical prior art implementation of an NPWT device, a pressure sensor is connected to the control unit and generating data that is used by the control unit for determining a value for the negative pressure formed by the negative pressure pump. The control unit then uses this pressure value for controlling when and how to activate the negative pressure pump, typically for ensuring that the negative pressure stays within a predefined negative pressure range, where the predefined negative pressure range forms part of the predefined operational range for the NPWT device. One problem with such an implementation is that if the control unit fails in the processing of the data from the pressure sensor, or if the control unit "hangs", then it may be possible that the negative pressure pump stays activated even if the negative pressure goes outside of the predefined negative pressure range. This could potentially inflict pain to the patient, typically at the wound site, since the negative pressure at the wound site in such a situation potentially could be well below what is suitable for the wound.

To counteract such a situation, it may in one embodiment be advantageous to instead arrange the pressure sensor to be directly connected to the external control circuitry, and adapt the logic of e.g. the controllable switch comprised with the external control circuitry to switch off the controllable switch if the pressure sensor provides an indication that the negative pressure is outside of the predefined negative pressure range.

To handle differences between different batches of pressure sensors it may be advantageous to adapt the pressure sensor and/or the NPWT device to comprise calibration circuitry. By means of such an implementation it could be possible to e.g. allow each individual pressure sensor to be calibrated at a production stage of the NPWT device. In some embodiments the pressure sensor is a differential pressure sensor, allowing for further reliability as to the measurement data provided by the pressure sensor.

In some embodiment of the present disclosure it may be advantageous to further equip the NPWT device with a watchdog circuitry, connected to and arranged as an external component in relation to the control unit. The watchdog circuitry is typically provided for allowing a path of recovery of the control unit in case of a malfunction of the control unit. The watchdog circuitry generally comprises a timer that is arranged to reset the control unit once the timer has counted down to zero (from a present value defining a preset time). However, as long as the control unit is functioning in a normal manner, the control unit will continuously (before the present time has passed) reset the timer of the watchdog circuitry, whereby the watchdog circuitry will not reset the control unit.

However, in accordance to the present disclosure the watchdog circuitry is not only arranged in connection with the control unit and provided for "resetting" the control unit. Rather, in accordance to the present disclosure the watchdog circuitry is also connected to the first controllable switch, whereby a "timeout" of the timer comprised with the watchdog circuitry will also switch the first controllable switch. Such an implementation will in an advantageous manner further enhance the security of the NPWT device, since the preset time of the watchdog circuitry may be set short enough (e.g. possibly between 0.5 second to 2 seconds) to ensure that the operation of the negative pressure pump is terminated in a direction connection with a possible malfunction of the control unit.

Accordingly, in addition (or instead) of waiting for the negative pressure to go outside of the predefined negative pressure range, the switching of the first controllable switch achieved by the watchdog circuitry in conjunction with the first controllable switch of the external control circuitry will add a further limitation to an unwanted operation of the negative pressure pump in case of failure of the NPWT device, thus further reducing the risks involved with using the NPWT device in accordance to the present disclosure.

In one embodiment of the present disclosure the control circuitry further comprises a second controllable switch connected to the control unit and adapted to switch on the power to the negative pressure pump if the negative pressure pump is to be operated. The control unit may thus effectively control when to operate the negative pressure pump, where the second controllable switch of the external control circuitry will function as a "buffer" between the control unit and the negative pressure pump, reducing the risk e.g. any disturbances generated by the negative pressure pump to affect the operation of the control unit.

Advantageously, the control unit is further adapted to control the second controllable switch using pulse width modulation (PWM), whereby a speed of the negative pressure pump may be seamlessly controlled according in accordance to a desired behavior/scheme.

In some embodiments of the present disclosure the control unit is adapted to continuously measure an intermediate voltage level of the battery, and to select the PWM scheme based on recently measured voltage level of the battery. Generally, the voltage level of the battery will gradually drop during operation of the NPWT device, and simply switching on/off the second controllable switch using a constant PWM switching scheme will result in a reduction of the speed of the negative pressure pump as the voltage level drops. Accordingly, to maintain an operational speed of the negative pressure pump within a predetermined speed range (e.g. +/−10% of a speed value), it is desirable to select the PWM scheme based on a recently measured voltage level of the battery. By such a measure it is possible to keep the speed of the negative pressure pump essentially constant (such as within the mentioned exemplary+/−10%). Keeping the speed of the negative pressure pump essentially constant will also result in a sound level of the negative pressure pump at an essentially constant level, reducing a disturbance of the patient using the NPWT device. In some embodiments a "base speed" of the negative pressure pump is selected during manufacturing or by the patient, where the base speed is set to a level where the patient experiencing (or is expected to experience) the least amount of disturbance. The selection of the base speed may in some embodiments be achieved by providing input from the patient using a user interface comprised with the NPWT device.

Furthermore, it may generally be preferred that the canister is detachably connected to a housing comprising the negative pressure pump, whereby e.g. a full canister may be removed and replaced with an empty (new) canister. In such an embodiment it may be desirable to provide e.g. the canister and the housing with some form of engagement means 204 for securing the canister to the housing such that the canister is not unintentionally removed from the housing. The engagement means may in one embodiment comprise a pair of flexible protrusions extending from the canister and adapted to engage with e.g. corresponding locking grooves provided at the housing.

In an embodiment of the present disclosure, the NPWT device is adapted for home care. Accordingly, in combination with the NPWT device being mobile, the NPWT device may be adapted to be carried by the user, e.g. in a pocket, or on a belt or strap (e.g., via clip 206). In addition, for simplifying the (end) user operation of the NPWT device, the NPWT device may additionally be provided with indication means for displaying a symbol providing an indication of an operational status for the NPWT device. In one embodiment the NPWT device may instead of display element be provided with dedicated light sources arranged at an operational front surface of NPWT device for providing the user with the mentioned operational status information.

Advantageously, the NPWT device is provided as a component of a wound treatment system, further comprising the wound cover. This will be further elaborated below in the detailed description of the present disclosure.

According to another aspect of the present disclosure, there is further provided a method of operating a mobile negative pressure wound therapy (NPWT) device, the NPWT device comprising a housing, a negative pressure pump arranged within the housing, a canister fluidly coupled to the negative pressure pump and to a wound cover, the wound cover provided for creating a sealed space defined in part by a wound site, a battery arranged within the housing, and a control unit arranged within the housing, the control unit being electrically connected to the battery, wherein the method comprises the steps of operating the negative pressure pump by providing power from the battery to the negative pressure pump to establish a negative pressure within the sealed space, forming a first control signal if the NPWT device is determined to operate outside a predefined operational range, terminating the operation of the negative pressure pump using a control circuitry further comprised with the NPWT device and provided externally from the control unit. This aspect of the present disclosure provides similar advantages as discussed above in relation to the previous aspects of the present disclosure.

According to a still further aspect of the present disclosure there is provided a computer program product comprising a non-transitory computer readable medium having stored thereon computer program means for operating a mobile negative pressure wound therapy (NPWT) device, the NPWT device comprising a housing, a negative pressure pump arranged within the housing, a canister fluidly coupled to the negative pressure pump and to a wound cover, the wound cover provided for creating a sealed space defined in part by a wound site, a battery arranged within the housing, and a control unit arranged within the housing, the control unit being electrically connected to the battery, wherein the computer program product comprises code for operating the negative pressure pump by providing power from the battery to the negative pressure pump to establish a negative pressure within the sealed space, code for forming a first control signal if the NPWT device is determined to operate outside a predefined operational range, code for terminating the operation of the negative pressure pump using a control circuitry further comprised with the NPWT device and provided externally from the control unit. Also this aspect of the present disclosure provides similar advantages as discussed above in relation to the previous aspects of the present disclosure.

Further features of, and advantages with, the present disclosure will become apparent when studying the appended claims and the following description. The skilled addressee realizes that different features of the present disclosure may be combined to create embodiments other than those described in the following, without departing from the scope of the present disclosure.

BRIEF DESCRIPTION OF THE DRAWINGS

The various aspects of the present disclosure, including its particular features and advantages, will be readily understood from the following detailed description and the accompanying drawings, in which.

DETAILED DESCRIPTION

Figure 1:
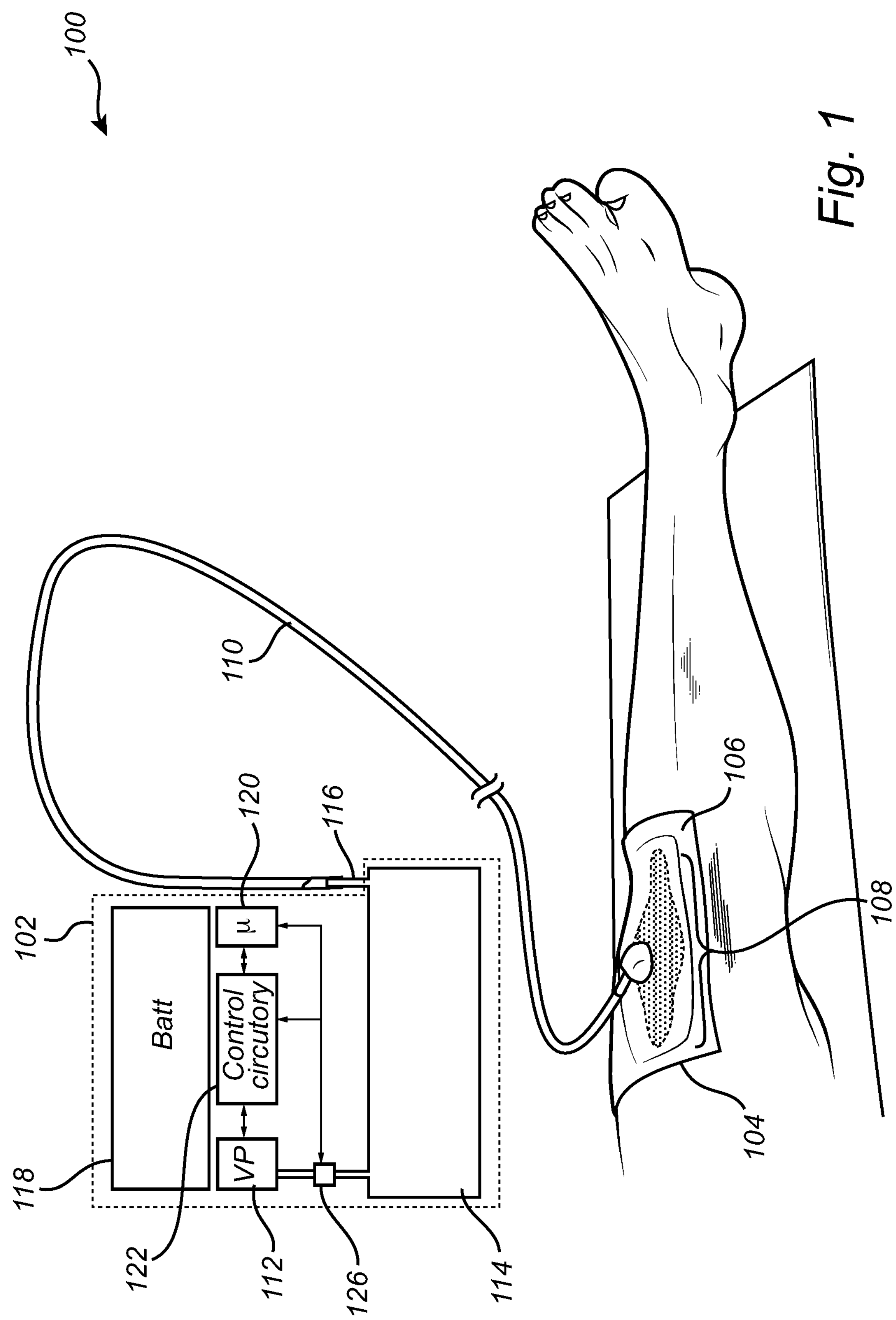
FIG. 1 conceptually illustrates a wound treatment system comprising an NPWT device according to the present disclosure.

The present disclosure will now be described more fully hereinafter with reference to the accompanying drawings, in which currently preferred embodiments of the present disclosure are shown. The present disclosure may, however, be embodied in many different forms and should not be construed as limited to the embodiments set forth herein; rather, these embodiments are provided for thoroughness and completeness, and fully convey the scope of the present disclosure to the skilled person. Like reference characters refer to like elements throughout.

Turning now to the drawings and to FIG. 1 in particular, there is conceptually illustrated a wound treatment system 100, comprising a NPWT device 102 in accordance with the present disclosure. The wound treatment system 100 further comprises a wound cover 104, the wound cover 104 being adapted to create a sealed space 106 defined in part by a wound surface 108, such as at the skin of a user/person, at or around a wound of the user/person. Additionally, the NPWT device 102 is fluidly connected to the wound cover 104 using e.g. a tubing 110. The tubing 110 may be of any suitable flexible tubing fabricated from elastomeric and/or polymeric materials.

The NPWT device 102 in turn comprises a negative pressure pump 112 adapted for establishing a negative pressure when the negative pressure pump 112 is operable, i.e. in an active state. The negative pressure pump 112 may be any type of pump that is biocompatible and maintains or draws adequate and therapeutic vacuum levels. Preferably, the negative pressure level to be achieved is in a range between about −20 mmHg and about −300 mmHg. In a possible embodiment of the present disclosure, a negative pressure range between about −80 mmHg and about −140 mmHg is used. In a possible embodiment of the present disclosure, the negative pressure pump 112 is either a diaphragm pump or a peristaltic pump, or the like, in which the moving parts draw the mentioned fluid from the wound cover 104.

The negative pressure pump 112 is fluidly connected to a canister 114, the canister 114 also forming part of the NPWT device 102. The canister 114 may be formed from e.g. molded plastic or the like, and possibly being a detachable component of the NPWT device 102. As mentioned above, the canister 114 is preferably at least partly transparent/translucent to permit viewing into the interior of the canister 114 to assist the user in determining the remaining capacity of the canister 114.

For ease of understanding of the following discussion of the present disclosure, it should be understood that the expressions "negative pressure", "sub-atmospheric pressure", "reduced pressure", as used interchangeably herein, generally refer to a pressure less than a local ambient pressure, such as the ambient pressure in a local environment external to a sealed therapeutic environment provided by a wound cover or dressing. In many cases, the local ambient pressure may also be the atmospheric pressure at which a patient is located. Unless otherwise indicated, values of pressure stated herein are gauge pressures. Similarly, references to increases in negative pressure typically refer to a decrease in absolute pressure, while decreases in negative pressure typically refer to an increase in absolute pressure.

An inlet port 116 is formed at the canister 114, for allowing connection to the tubing 110. The inlet port 116 may also be formed elsewhere at the NPWT device 102, however still fluidly connected to the canister 114. The connection between the inlet port 116 and the tubing 110 is a sealed connection, thus ensuring that no leakage is formed at the inlet port 116 during normal operation of the NPWT device 102. The tubing 110 is preferably releasably connected to the inlet port 116 through conventional means including a friction fit, bayonet coupling, snap fit, barbed connector, or the like. The inlet port 116 may be molded/formed from the same material and/or at the same time as forming the canister 114.

The NPWT device 102 further comprises a battery 118 for powering the NPWT device 102. The battery 118 may preferably be of the rechargeable type but may alternatively be arranged to be disposable and thus to be changed once discharged. A specifically adapted battery pack may be used in relation to some embodiment of the present disclosure.

The NPWT device 102 also comprises a control unit 120, electrically connected to the battery 118 and adapted to control an operation of the negative pressure pump 112. The control unit 120 may include a microprocessor, microcontroller, programmable digital signal processor or another programmable device. The control unit 120 may also, or instead, each include an application specific integrated circuit, a programmable gate array or programmable array logic, a programmable logic device, or a digital signal processor. Where the control unit 120 includes a programmable device such as the microprocessor, microcontroller or programmable digital signal processor mentioned above, the processor may further include computer executable code that controls operation of the programmable device.

In line with the present disclosure, the NPWT device 102 further comprises a control circuitry 122 provided externally from the control unit 120 and arranged to generally control the operation of the negative pressure pump 112, specifically for ensuring that the operation of the negative pressure pump 112 may be swiftly terminated in case the NPWT device 102 starts to operate outside of what is considered to be a normal behavior, as has been discussed above. The operation of the control circuitry 122 is further elaborated below in relation to FIG. 3.

In addition, the NPWT device 102 comprises at least one pressure sensor 126 arranged in fluid connection with the negative pressure pump 112.

During use of the NPWT device 102, the wound cover 104 is arranged at a wound site of the user/patient, forming the sealed space 106. The tubing 110 is provided to fluidly connect the wound cover 104 to the inlet port 116 of the NPWT device 102. The NPWT device 102 is then activated, e.g. by the user/patient, by pressing the start/pause button 208 (see FIG. 2A). The negative pressure pump 112 is thereby activated. When activated, the negative pressure pump 112 will start to evacuate air through the canister 114, the inlet port 116, the tubing 110 and the sealed space 106 formed by the wound cover 104. Accordingly, the negative pressure will be created within the sealed space 106. In case a liquid has been formed at the wound site, this liquid from the wound site may at least partly be "drawn" from the wound site, through the tubing 110, the inlet port 116 and into the canister 114. The amount of liquid (possibly defined as exudate) that is drawn from the wound and collected in the canister will depend on the type of wound that is being treated as well as the type of wound dressing used. For example, in case an absorbent dressing is used, the liquid may be absorbed and collected both in the canister and the wound dressing, whereas if a dressing with no or little absorption capacity is used most or all of the liquid from the wound site may be collected in the canister. A suitable filter member (not shown in FIG. 1) is arranged between the canister 114 and the negative pressure pump 112 to ensure that no fluid is allowed to pass to the negative pressure pump 112 from the canister 114.

Figures 2A, 2B:
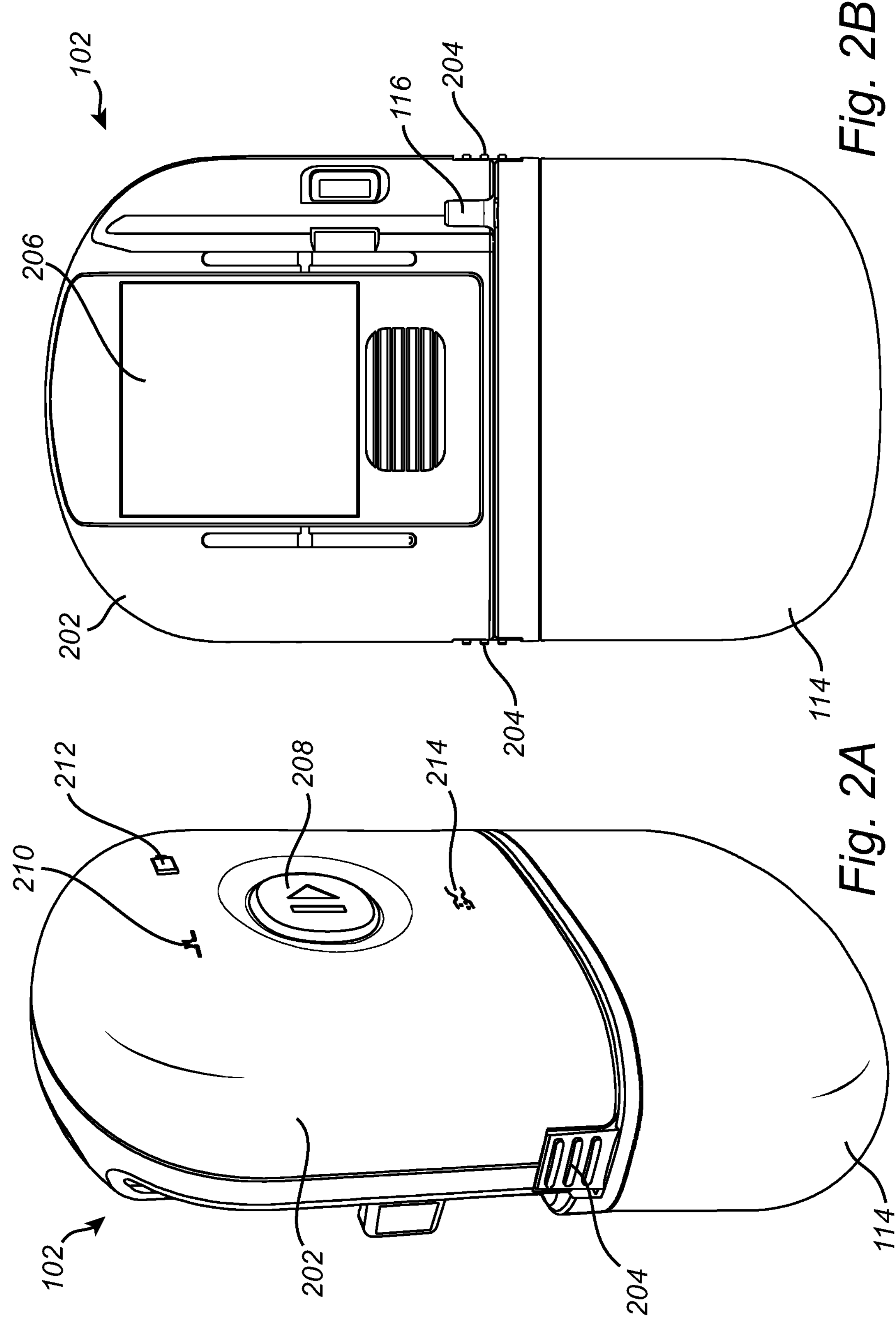
FIGS. 2A and 2B show different views of a possible implementation of the NPWT device shown in FIG. 1.

Turning now to FIGS. 2A and 2B illustrating different views of a possible implementation of the NPWT device according to the present disclosure, as shown in FIG. 1. As presented, a majority of the components comprised with the NPWT device 102 are arranged within a housing 202, where the housing 202 may be formed at least partly from plastic.

As presented above, the canister 114 is preferably allowed to be detachably connected to the housing 202. By means of such an implementation it may be possible for the user operating the NPWT device 102 to remove and e.g. discard the canister 114 in case the canister 114 is full or otherwise need to be exchanged (e.g. due to a problem with the canister 114 or the inlet port 116, etc.).

As shown in FIG. 2A, the housing 202 is provided with a start/pause button 208 for initiating/pausing operation of the NPWT device 102. The start/pause button 208 is electrically connected to the control unit 120. In addition, the housing 202 may optionally be provided with one or a plurality of display symbols 210, 212, 214 for providing feedback to the user of the NPWT device 102. For example, the display symbols 210, 212, 214 may provide an indication to the user that there is a possible leakage at e.g. the wound cover 104, that there is a need to charge/change the battery 118, or that there is a blockage in the tubing 110. The display symbols 210, 212, 214 may possible be formed by providing e.g. LEDs below an inner surface of the housing 202, where suitable symbols may be formed, e.g. printed, at an outer surface of the housing 202 at suitable corresponding positions. It should be understood that the display symbols 210, 212, 214 alternatively may be shown on a display screen integrated with the housing 202.

Figure 3:
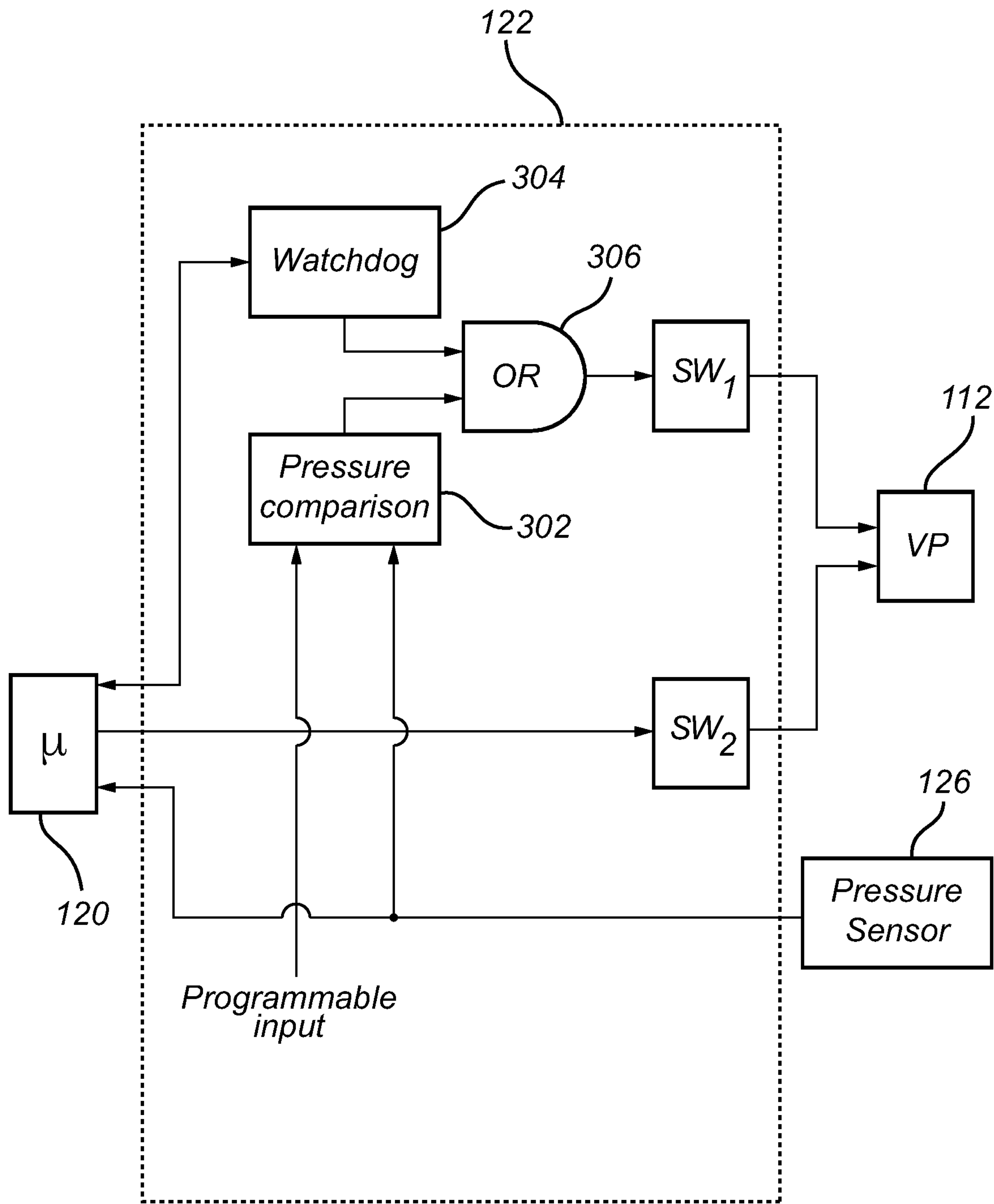
FIG. 3 shows a detailed exemplary implementation of a control circuitry comprised with the NPWT device according to the present disclosure.

Turning now to FIG. 3, presenting an exemplary detailed schematic of the control circuitry 122 comprised with the NPWT device 102. As discussed above, the control circuitry 122 is provided externally and separately from the control unit 120, however arranged in communication with the control unit 120. The control circuitry 122 is further arranged in communication with the pressure sensor 126 and the negative pressure pump 112

The control circuitry 122 comprises components allowing the operation of the negative pressure pump 112 to be terminated without any involvement of the control unit 120. Thus, even in a situation where the control unit 120 fails to correctly identify e.g. a problem with sensor values received (such as a "too low" negative pressure), the control circuitry 122 can act independently of the control unit 120 and turn off the negative pressure pump 112.

In the non-limiting and exemplary illustration as shown in FIG. 3, the control circuitry 122 is shown to comprise a first controllable switch $SW_1$. When the first controllable switch $SW_1$ is deactivated the negative pressure pump 112 will be turned off. The first controllable switch $SW_1$ is in turn controlled by each one of a pressure comparator 302 and a watchdog circuitry 304, both comprised with the control circuitry 122. Accordingly, the negative pressure pump 112 will be turned off by means of the first controllable switch $SW_1$ if either of the pressure comparator 302 or the watchdog 304 provides a control signal indicating that the operation of the negative pressure pump 112 is to be terminated. In FIG. 3 the "either functionality" is functionally illustrated by a logic OR circuitry 306.

The pressure comparator 302 is in turn connected to the pressure sensor 126, where data from the pressure sensor is compared to a predetermined negative pressure range. The predetermined negative pressure range may in turn be set e.g. a time of manufacturing, allowing the pressure sensor 126 to be correctly and possibly individually calibrated in a calibration process. It may in some embodiments be suitable to allow the pressure sensor 126 to be implemented as a differential pressure sensor, in some embodiments allowing for an in comparison higher reliability as compared to non-differential pressure sensor. As is shown in FIG. 3, the pressure comparator 302 is provided with an interface for receiving the predetermined negative pressure range. Such an interface may for example be configured in line with suitable communication protocols, where the so called I2C protocol may be useful.

Accordingly, in case the pressure value as determined by the pressure sensor 126 fall outside of the predetermined negative pressure range, the pressure comparator 302 generates a control signal for controlling the first controllable switch $SW_1$, whereby the first controllable switch $SW_1$ is turned off and the operation of the negative pressure pump 112 is terminated. It should be understood that the pressure value as determined by the pressure sensor 126 is also provided to the control unit 120, for use in the general operation of the NPWT device 102.

The watchdog circuitry 304 is arranged in communication with the control unit 120 and is generally comprised with the NPWT device 102 for allowing path of recovery of the control unit 120 in case of a malfunction of the control unit 120. However, in line with the present disclosure the watchdog circuitry 304 will also function as a means for direct terminating the operation of the negative pressure pump 112. This is achieved by allowing a "reset signal" (in case of a non-responsive control unit 120) to be siphoned off and provided to the first controllable switch $SW_1$, i.e. not just for provided to the control unit 120 for resetting the control unit 120. Accordingly, if the watchdog circuitry 304 enters into a reset state, the reset signal will reset the control unit 120 and at the same time provide a control signal for operating the first controllable switch $SW_1$.

The implementation of the watchdog circuitry 304 in relation to the first controllable switch $SW_1$ allows for a greatly reduced reaction time as compared to a situation where the termination of the negative pressure pump 112 is only dependent on the operation of the control unit 120. That is, rather than having to wait for the control unit 120 to "reboot", the watchdog circuitry 304 will directly provide its control signal to the first controllable switch $SW_1$ to terminate the operation of the negative pressure pump 112.

In addition to the above, the control circuitry 122 further comprises a second controllable switch $SW_2$. The second controllable switch $SW_2$ is arranged in communication with the control unit 120 and may in some embodiments be seen as functioning as driver for the negative pressure pump 112. In some implementations of the present disclosure, the control unit operates the negative pressure pump 112 based on pulse width modulation (PWM), meaning that the control unit 112 switches the negative pressure pump 112 on and off, using the second controllable switch $SW_2$. The frequency of the switching is selected to be high enough to ensure that the moment of inertia of an electrical motor (not shown) comprised with the negative pressure pump 112 continues to operate the negative pressure pump 112. However, by controlling the ratio between the time the second controllable switch $SW_2$ on and off, the overall suction provided by means of the negative pressure pump 112 may be controlled.

In some embodiments it may be desirable to select a PWM switching scheme that keeps the frequency fairly constant over time. In such an embodiment it is thus desirable to keep the frequency fairly constant while at the same time adjusting the on/off ratio (as compared to adjust both of the switching frequency and the on/off ratio). Such an implementation has shown desirable for the end user, since this keeps any sound stemming from the operation of the negative pressure pump 112.

To achieve such a functionality, it may in some embodiments be desirable to monitor a voltage level of the battery 118 and select the PWM switching scheme according to a recently measured voltage level. By means of such an implementation, it may be possible to keep the speed of the negative pressure pump 112 even though the voltage level of the battery 118 will gradually decline over time.

Figure 4:
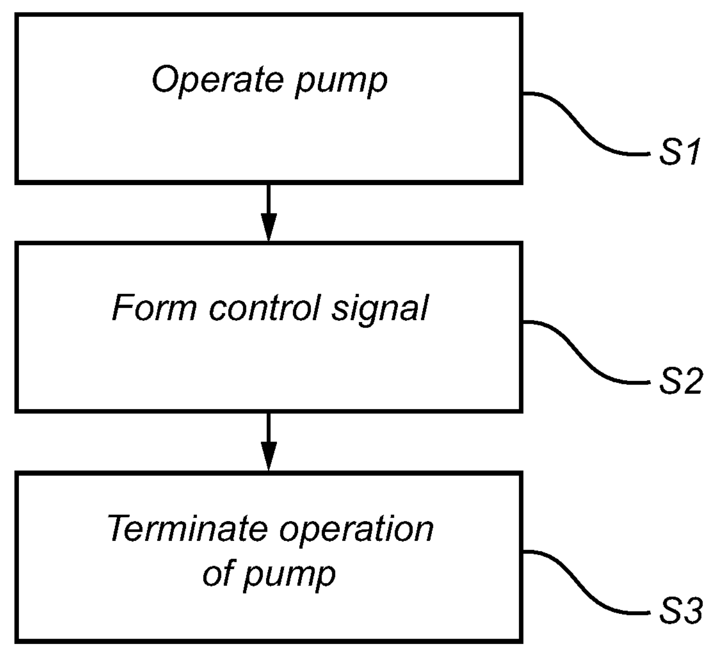
FIG. 4 is a flow chart illustrating the steps of performing the method according to a currently preferred embodiment of the present disclosure, for operating the present NPWT device.

During operation of the NPWT device 102, with further reference to FIG. 4, the control unit will select a suitable PWM scheme, for example based on recently measured voltage level of the battery 118, and subsequently generate a control signal that in turn controls the second controllable switch $SW_2$, thereby operating, S1, the negative pressure pump 112.

The control unit 120 will continuously receive an indication from the pressure sensor 126 relating to the negative pressure formed by the negative pressure pump 112, and control when and for how long time the negative pressure pump 112 is to operate. However, in line with the present disclosure it is desirable to ensure that the operation of the negative pressure pump 112 in case of any possible problem with the NPWT device 102.

Accordingly, in line with the present disclosure a control signal is formed, S2, if the NPWT device 102 is determined to operate outside a first predefined operational range. Operation outside of first predefined operational range for example includes a situation where the negative pressure formed by the negative pressure pump 112 comes outside a predetermined negative pressure range. However, other situations include for example where the control unit 120 of the NPWT device 102 is determined to fail, such as by a reset signal generated by the watchdog circuitry 304 comprised with the control circuitry 122. Also in this situation such a control signal is formed.

The control signal is in turned used for terminating, S3, the operation of the negative pressure pump 112 using the control circuitry 122, where the control circuitry 122 is provided externally from the control unit 120.

The control functionality of the present disclosure may be implemented using existing computer processors, or by a special purpose computer processor for an appropriate system, incorporated for this or another purpose, or by a hardwire system. Embodiments within the scope of the present disclosure include program products comprising machine-readable medium for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor.

Although the figures may show a sequence, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps and decision steps. Additionally, even though the present disclosure has been described with reference to specific exemplifying embodiments thereof, many different alterations, modifications and the like will become apparent for those skilled in the art.

In addition, variations to the disclosed embodiments can be understood and effected by the skilled addressee in practicing the present disclosure, from a study of the drawings, the disclosure, and the appended claims. Furthermore, in the claims, the word “comprising” does not exclude other elements or steps, and the indefinite article “a” or “an” does not exclude a plurality.

The invention claimed is:

1. A mobile negative pressure wound therapy (NPWT) device, comprising:

a housing, a negative pressure pump arranged within the housing, a canister fluidly coupled to the negative pressure pump and to a wound cover, the wound cover provided for creating a sealed space defined in part by a wound site, a battery arranged within the housing, and a control unit arranged within the housing, the control unit being electrically connected to the battery and adapted to provide power to the negative pressure pump for operating the negative pressure pump to establish a negative pressure within the sealed space, wherein the NPWT device further comprises control circuitry provided externally from the control unit and adapted to receive, directly from a pressure sensor, a signal corresponding to a pressure measurement, wherein the control circuitry is configured to terminate the operation of the negative pressure pump independently of the control unit if the NPWT device is determined to operate outside of a predefined negative pressure range.

2. The NPWT device according to claim 1, wherein the control circuitry further comprises a first controllable switch arranged to switch off the power to the negative pressure pump to terminate thereby the operation of the negative pressure pump.

3. The NPWT device according to claim 2, wherein the first controllable switch comprises a first input control line for controlling the controllable switch.

4. The NPWT device according to claim 3, further comprising a watchdog circuitry connected to both of the control unit and the first input control line of the first controllable switch, wherein a timeout of the watchdog switches the controllable switch.

5. The NPWT device according to claim 3, further comprising a pressure sensor adapted to provide an indication of the negative pressure formed by the negative pressure pump, wherein, upon receiving the indication of the negative pressure being outside the predefined negative pressure range, the control circuitry is configured to switch the first controllable switch.

6. The NPWT device according to claim 2, wherein the control circuitry comprises a second controllable switch connected to the control unit and adapted to switch on the power to the negative pressure pump if the negative pressure pump is to be operated.

7. The NPWT device according to claim 6, wherein the control unit is further adapted to control the second controllable switch using pulse width modulation (PWM).

8. The NPWT device according to claim 7, wherein the control unit is further adapted to select a PWM scheme based on a recently measured voltage level of the battery.

9. The NPWT device according to claim 8, wherein the PWM scheme is further selected to maintain an operational speed of the negative pressure pump within a predetermined speed range.

10. A wound treatment system, comprising:

an NPWT device according to claim 1, and a wound cover.

11. A method of operating a mobile negative pressure wound therapy (NPWT) device, the NPWT device comprising:

a housing, a negative pressure pump arranged within the housing, a canister fluidly coupled to the negative pressure pump and to a wound cover, the wound cover provided for creating a sealed space defined in part by a wound site, a battery arranged within the housing, and a control unit arranged within the housing, the control unit being electrically connected to the battery, wherein the method comprises the steps of:

operating the negative pressure pump by providing power from the battery to the negative pressure pump to establish a negative pressure within the sealed space, providing, directly from a pressure sensor, a signal corresponding to a pressure measurement to control circuitry further comprised with the NPWT device and provided externally from the control unit in response to the first control signal, forming a first control signal by the control circuitry if the NPWT device is determined to operate outside a first predefined negative pressure range, terminating the operation of the negative pressure pump independently of the control unit using the control circuitry.

12. The method according to claim 11, wherein the control circuitry further comprises a first controllable switch arranged to receive the first control signal at first input control line of the first controllable switch and to switch off the power to the negative pressure pump to terminate thereby the operation of the negative pressure pump.

13. The method according to claim 12, wherein the NPWT device further comprises a watchdog circuitry connected to both of the control unit and the first input control line of the first controllable switch, and the watchdog circuitry is adapted to form a control signal at a timeout of the watchdog, the method further comprising terminating the operation of the negative pressure pump in response to the control signal at the timeout of the watchdog.

14. The method according to claim 12, wherein the NPWT device further comprises a pressure sensor adapted to provide an indication of the negative pressure formed by the negative pressure pump, and the first control signal is formed if the indication of the negative pressure is determined to be outside the predefined negative pressure range.

15. The method according to claim 12, wherein the NPWT device further comprises a second controllable switch connected to the control unit and adapted for providing the power to the negative pressure pump, and the method further comprises the step of:

switching on the second controllable switch according to a pulse width modulation (PWM) scheme.

16. The method according to claim 15, further comprising the steps of:

measuring a battery level, and selecting the PWM scheme based on the battery level.

17. A non-transitory computer readable medium having stored thereon computer program instructions for:

operating a negative pressure pump of a mobile negative pressure wound therapy (NPWT) device by providing power from a battery to the negative pressure pump to establish a negative pressure within a sealed space and controlling the negative pressure with a control unit, forming, by control circuitry further comprised with the NPWT device and provided externally from the control unit, based on a signal provided directly from a pressure sensor to the control circuitry, a first control signal if the NPWT device is determined to operate outside a predefined negative pressure range, and terminating the operation of the negative pressure pump independently of the control unit using the control circuitry in response to the first control signal, the NPWT device comprising:

a housing, the negative pressure pump arranged within the housing, a canister fluidly coupled to the negative pressure pump and to a wound cover, the wound cover provided for creating a sealed space defined in part by a wound site, the battery arranged within the housing, and the control unit arranged within the housing, the control unit being electrically connected to the battery.

* * * * *